United States Patent [19]

Ozaki et al.

[11] Patent Number: 4,489,721
[45] Date of Patent: Dec. 25, 1984

[54] DOUBLE LUMEN TUBE ADAPTOR AND VALVE SYSTEM FOR MEDICAL ANESTHESIA CIRCUITS

[75] Inventors: George T. Ozaki; Jonathan L. Benumof, both of San Diego; Henrik W. Andersen, Del Mar, all of Calif.

[73] Assignee: The Regents of the University of California, Berkeley, Calif.

[21] Appl. No.: 454,580

[22] Filed: Dec. 30, 1982

[51] Int. Cl.³ .......................................... A61M 16/00
[52] U.S. Cl. .................................. 128/205.24; 137/597
[58] Field of Search ............... 128/200.14, 200.19, 128/200.21, 201.28, 203.12, 203.25, 203.28, 203.29, 204.18, 205.24, 910, 912, 911, 207.16; 604/32, 248; 137/597

[56] References Cited

U.S. PATENT DOCUMENTS

| | | | |
|---|---|---|---|
| 883,987 | 4/1908 | Teter | 128/203.28 |
| 1,683,723 | 9/1928 | Myres | 604/32 |
| 2,441,483 | 5/1948 | Goehring | 137/597 |
| 2,791,217 | 5/1957 | Iskander | 128/205.24 |
| 3,942,547 | 3/1976 | Pfitzner | 137/102 |
| 4,177,830 | 12/1979 | Munson | 137/501 |
| 4,239,039 | 12/1980 | Thompson | 128/205.24 |
| 4,253,453 | 3/1981 | Hay | 128/200.19 |
| 4,291,689 | 9/1981 | Hay | 118/200.24 |

FOREIGN PATENT DOCUMENTS

| | | | |
|---|---|---|---|
| 549005 | 10/1956 | Italy | 128/205.24 |
| 9583 | of 1911 | United Kingdom | 128/203.25 |
| 534942 | 3/1941 | United Kingdom | 128/205.24 |
| 537476 | 6/1941 | United Kingdom | 137/597 |

OTHER PUBLICATIONS

White, G. M. J.: A two way union for double-lumen tubes. Anaesthesia 15:77–79, 1980.
Tanguturi S., Capan L. M., Patel K.; et al.: A New Double Lumen Tube Adaptor, Anesth Analg (Cleve) 59: pp. 507–508, 1980.
Welsh B. E., Conn A. W.: A Catheter Mount For Double-Lumen Endobronchial Tubes, Can Anaesth Soc J 17: pp. 183–186, 1970.
Salt, R. H.: A Modified Two Way Union for Double-Lumen Tube, Anaesthesia 25: pp. 418–419, 1970.
Viljoen, J. F.: A New Double-Lumen Endotracheal Tube Connector, Anesthesiology 28: pp. 950–951, 1967.

Primary Examiner—Henry J. Recla
Attorney, Agent, or Firm—Brown, Martin & Haller

[57] ABSTRACT

A double lumen tube adaptor and valve control system for lung anesthesia includes a housing having a pair of outlet ports with a pair of inlet ports aligned with the outlet ports and a common central inlet port communicating with a central passageway that is controllable by two separate valves for selectively communicating the common inlet port with both outlet ports, one outlet port for communicating the in line outlet and inlet ports.

10 Claims, 7 Drawing Figures

U.S. Patent        Dec. 25, 1984        4,489,721
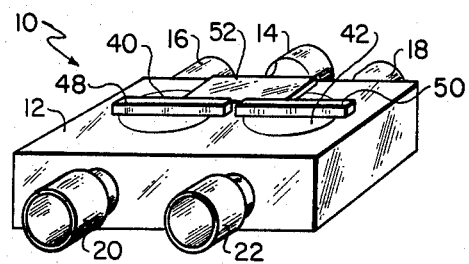
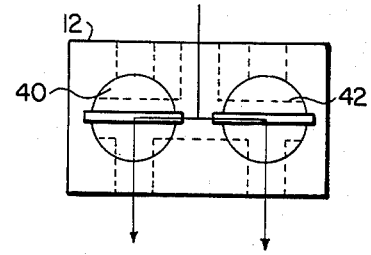
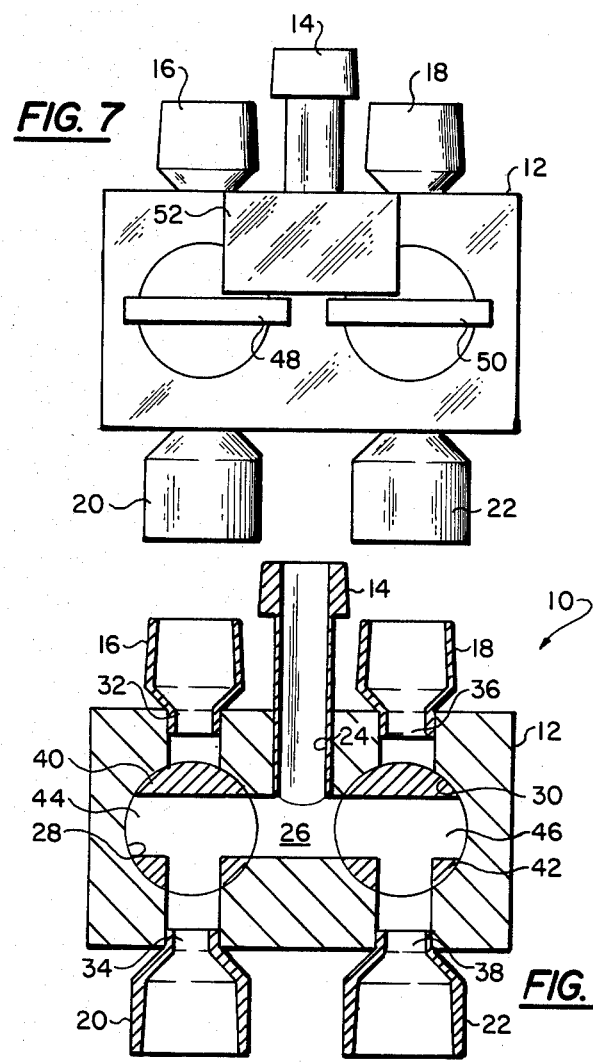
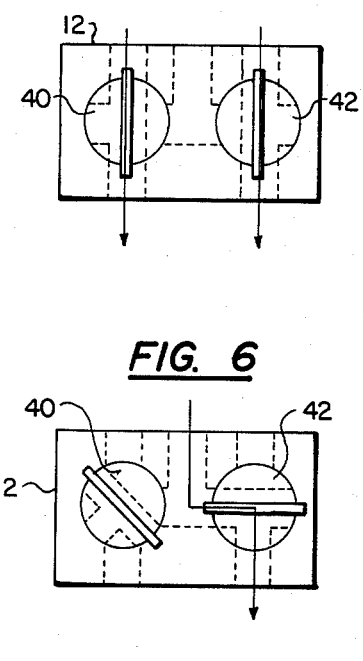
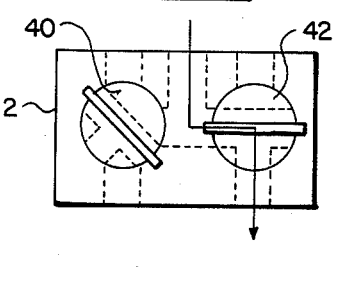

DOUBLE LUMEN TUBE ADAPTOR AND VALVE SYSTEM FOR MEDICAL ANESTHESIA CIRCUITS

BACKGROUND OF THE INVENTION

The present invention relates to anesthesia machines and pertains particularly to a double lumen tube adaptor and valve system for such machines.

One lung anesthesia has gained wide acceptance in recent years because it can be used to isolate a normal lung from a contaminated lung and also provide a motionless surgical field. Double lumen tube adaptors which have been designed originally for bronchospirometric studies have been found to be useful in anesthesia for thoracic surgery. Considerable improvements have been made in such tubes in recent years which afford independent control of each lung so that transbronchial spillover can be eliminated and ventilation difficulties in certain cases, such as valvular pneumothorax, bronchial fistula, and tension cysts can be avoided.

Double lumen connectors and adaptors have been developed which eliminates many of the problems with prior equipment which required disconnecting of and clamping off of rubber tubing and the resultant difficulties of attaching and detaching rubber tubing and the like. These prior art devices permit the application of three (3) major one lung ventilation/anesthesia functions; including ventilation, exposure of one lung to atmospheric pressure, and suctioning of one lung at a time. However, none of these prior art devices have the capability of providing the application of three (3) recent major advances in the management of one lung ventilation/anesthesia; one lung positive end-expiratory pressure (PEEP) with or without tidal ventilation, differential PEEP to both lungs, and one lung fiberoptic bronchoscopy.

While the prior art developments have provided many useful improvements, further developments and improvements permitting all six (6) of the above described functions in a single unit are desirable.

SUMMARY AND OBJECTS OF THE INVENTION

It is therefore the primary object of the present invention to provide an improved double lumen tube adaptor for anesthesia systems.

In accordance with the primary aspect of the present invention, a double lumen tube adaptor assembly including a valve system includes a housing having a plurality of inlet ports including a common central port and outlet ports connectable by separate valve means to the common inlet ventilation port with the outlet ports and with the valves positionable to connect in line inlet ports that are in line with the outlet ports for ventilation, utilizing fiberoptic scopes, suction tubes and other instruments.

BRIEF DESCRIPTION OF THE DRAWINGS

The above and other objects and advantages of the present invention will become apparent from the following description when read in conjunction with the drawings wherein:

FIG. 1 is a perspective view of a preferred embodiment of the invention.

FIG. 2 is a section view of the embodiment of FIG. 1.

FIGS. 3 through 6 are schematic illustrations of showing the various valve positions for the embodiment of FIG. 1.

FIG. 7 is a top view of the embodiment of FIG. 1.

DETAILED DESCRIPTION OF A PREFERRED EMBODIMENT

Referring to FIG. 1 of the drawing, a double lumen tube adaptor and valve system is illustrated and designated generally by the numeral 10. This unit 10 comprises a housing 12 of a generally box-like configuration constructed of a suitable heat and solvent resistant material such as a plastic commonly sold under the trademark DELRIN. The housing includes a plurality of inlet or entry ports consisting of a central port 14 and outer or lateral ports 16 and 18. These ports connect with internal passages and by way of valve means with outlet ports 20 and 22. The inlet ports are on the machine side of the connection or adaptor and the outlet ports are on the patient's side of the adaptor. The inlet ports are male connectors of a standard anesthesia tapered male connectors of 15 millimeter with the outlet ports 15 millimeter female connectors being of the standard anesthesia tapered connectors.

Turning to FIG. 2, the housing includes a plurality of passageways connecting the various ports through the valve system. The central inlet port 14 communicates by way of a passage 24 with a central transverse passage 26 which communicates with valve bores 28 and 30. The valve bores 28 and 30 are at the center of aligned passages 32, 34 which connect the inlet port 16 with outlet port 20 and with pasage 36 and 38 which connect inlet port 18 with outlet or exit port 22. A three-way valve stem or plug 40 is positioned or mounted within the valve bore 28 and acts to selectively communicate either the central inlet port 14 with outlet port 20 or inlet port 16 with outlet port 20 or to completely close off the outlet port 20.

A similar valve member 42 is mounted within the valve bore 30 and functions to either connect the inlet port 14 with outlet port 22 or the inlet port 18 with outlet port 20 or to completely cutoff and close off the outlet port 22.

The valve stems or plugs 40 and 42 are three-way valves and, in the illustrated embodiment, each have a T-shaped passage network 44, 46 therethrough, respectively. The valve plugs 40 and 42 each include a handle 48 and 50 and function and are controllable for performing the selected function upon rotation of only 90°. A stop and retainer plate 52 mounted on top of the valve body (FIG. 1) retains the valve plugs 40 and 42 in their respective bores and provides stop means for limiting the rotation of the plugs to 90°.

This invention or unit as illustrated provides a single unit double lumen tube adaptor for six (6) one lung ventilation/anesthesia functions or options by simple rotation of one or more dials. This eliminates the need for external clamps and the need for connecting and disconnecting hoses and couplings. These six (6) options are: exposure to atmospheric pressure, suctioning, fiberoptic bronchoscopy, one lung positive end-expiratory pressure (PEEP), differential lung PEEP, and independent lung ventilation. These same lung functions or options can also be performed when the stopcock passage channels join both lateral entry ports with the corresponding exit ports as shown in FIG. 5. Turning to FIG. 3, the selector valves are turned to a setting for communicating the central inlet port 14 with both outlet ports 20, 22. This provides for both lung ventilation and/or PEEP of the lungs. This setting also permits the technically most complex maneuver, differential lung PEEP to be easily performed. This is performed by applying a different amount of PEEP to the lateral inlet port 16 compared to the PEEP applied to the central inlet port 14 (from a conventional PEEP valve in the anesthesia machine system). The application of all of these one lung functions does not require ventilation of the other lung or the application of any clamps to the airway tubing.

Referring to FIG. 4, the valve 42 is left in its selected position communicating the inlet port 14 with the outlet or lung port 22 while valve 40 is rotated to the selected position for communicating port 16 with outlet port 20. This provides direct communication of a lateral inlet port 16 with an outlet port 20 and permits or provides for six (6) different single lung functions; exposure to atmospheric pressure, suctioning, fiberoptic bronchoscopy, one lung PEEP, differential lung PEEP, and independent lung ventilation.

Referring to FIG. 5, both valves are turned to the 90° ventilation position communicating the two outer or lateral inlet ports 16 and 18 directly with the outlet ports 20, 22. This setting also provides for the six (6) above described functions. This setting might be useful if more space is required by bulky external apparatus.

Turning to FIG. 6, the valves are set in a position such that valve 40 is positioned for a completely closing off the lung connected with port 20 while the lung connected with port 22 is connected to the inlet or ventilation port 14. The lung connected to port 20 becomes a closed nonventilated space whose gas composition is dependent upon the previous ventilatory history. This valve setting would be desirable when very brief periods of nonventilation are required either to check for air leaks (following inhalation or at high lung volumes) or to facilitate surgery (following exhalation or at low lung volumes).

This double lumen tube and valving unit provides an arrangement wherein any number of functions can be performed simultaneously and independently. This unit has the capability of providing for the application of three (3) recent major advances in the management of one lung ventilation/anesthesia. These include one lung positive end-expiratory pressure (PEEP) with or without tidal ventilation. Another function is differential PEEP to both lungs and also one lung fiberoptic bronchoscopy as previously pointed out. This single unit double lumen tube adaptor allows the easy application of all six (6) of the major one lung ventilation/anesthesia functions simply by turning a dial to the desired setting without the necessity of disconnecting and clamping hoses. The inlet and outlet ports and valve passageways including the passages through the valve plugs are large enough (8 millimeter ID) to easily permit passage of a 5.6 mm OD fiberoptic bronchoscope.

EXAMPLE

The following actual case report illustrates the versatility of the adaptor:

A 20 year old female, with angiographic proven right main pulmonary artery thrombosis, underwent pulmonary thromboembolectomy under high dose fentanyl (60 mg/kg)-oxygen anesthesia. With a single lumen endotracheal tube in place, fulminant hemorrhagic pulmonary edema occurred upon termination of cardiopulmonary bypass. Fiberoptic bronchoscopy revealed that the right lung was the sole source of the edematous fluid. The patient was placed back on cardiopulmonary bypass and a double lumen endotracheal tube was inserted and connected to the anesthesia machine using our double lumen tube adaptor. The lungs were demonstrated to be functionally separated from one another by simple sequential turning of the adaptor stopcocks to the 45° position (FIG. 6) during positive pressure ventilation. Cardiopulmonary bypass was terminated again, while a sodium nitroprusside drip was initiated, but fulminant, exclusively right lung hemorrhagic pulmonary edema resulted again. By simple turning of the right stopcock between the central and lateral machine side ports, from the horizontal (FIG. 3) to the vertical (FIG. 4) position, the patient could be suctioned every third or fourth uninterrupted positive pressure ventilation breath. In an attempt to decrease the rate of right lung edema formation, right lung PEEP (5 to 10 centimeters $H_2O$) was applied (FIG. 4), with and without tidal ventilation to the right lung by attachment of the appropriate external system to the right machine side entry port. The edema fluid formation markedly abated over the ensuing hour and the patient was ventilated throughout the rest of the operative period with differential lung PEEP and differential lung volumes. The patient was successfully extubated from the double lumen tube on postoperative day one.

While we have illustrated and described our invention by means of specific embodiments, it is to be understood that numerous changes and modifications may be made therein without departing from the spirit and scope of the invention as defined in the appended claims.

We claim:

1. A double lumen tube adaptor and valve assembly for lung anesthesia circuits, said assembly comprising:
   a housing,
   a central passageway in said housing,
   a pair of lateral passageways in said housing, a plurality of inlet ports in said housing including a pair of lateral ports each fluidically communicating with a separate one of said lateral passageways and a common inlet port fluidically communicating with said central passageway, each of said inlet ports including means adapted for connection to a medical anesthesia machine,
   a pair of outlet ports in said housing, each fluidically communicating with a separate one of said lateral passageways and separately aligned with a separate one of said lateral inlet ports, each of said outlet ports including means adapted for connection to a patient circuit patient, and
   a pair of valve members rotatably mounted in said housing in alignment with said central and lateral passageways, said valve members each including passage means selectively positionable to be in alignment with said central and lateral passageways for selectively communicating certain of said inlet ports with said outlet ports, said passage means when aligned with said lateral passageways defining a straight-through passage from said lateral inlet ports to said outlet ports.

2. The adaptor assembly of claim 1 wherein said common inlet port is disposed centrally of said pair of lateral inlet ports.

3. The adaptor assembly of claim 2 wherein said central passageway extends transversely to said inlet and outlet ports.

4. The adaptor assembly of claim 3 wherein said lateral inlet ports are connected by an aligned through passage with the respective outlet ports, and said valve members are each rotatably mounted within a bore in said housing intersecting one of said through passages and positionable to permit passage of a fiberoptic bronchoscope therethrough.

5. The adaptor assembly of claim 1 wherein said valve members each include a generally T-shaped passageway therethrough.

6. The adaptor assembly of claim 1 wherein each of said valve members is selectively positionable to a first position for communicating said common inlet port with one of said outlet ports and to a second position for communicating a lateral inlet port with the respective aligned outlet port.

7. The adaptor assembly of claim 6 wherein said lateral inlet ports are connected by an aligned through passage with the respective outlet ports, and said valve members are each rotatably mounted within a bore in said housing intersecting one of said through passages and positionable to permit passage of a fiberoptic bronchoscope therethrough.

8. The adaptor assembly of claim 7 wherein said valve members each include a generally T-shaped passageway therethrough.

9. A double lumen tube adaptor and valve assembly for lung anesthesia circuits, said assembly comprising:

a housing, a transverse central passageway in said housing, a pair of lateral passageways in said housing intersecting said central passageway, a plurality of inlet ports in said housing including a pair of lateral inlet ports each connected to a separate one of said central passageways and a common lateral inlet port connected to said central passageway, each of said inlet ports including means adapted for connection to a medical anesthesia machine, a pair of outlet ports in said housing, each connected to a separate one of said lateral passageways and each aligned with a separate one of said lateral inlet ports, each outlet port including means adapted for connection to a patient circuit, a pair of bores in said housing, each at the intersection of said central and lateral passageways, a pair of valve members, each rotatably mounted within a separate one of said bores, said valve members each including a generally T-shaped passageway therethrough being selectively positionable for alignment with said central and lateral passageways for selectively communicating said lateral inlet ports with said outlet ports, said T-shaped passageways when aligned with said lateral passageways defining a straight-through unobstructed passage from said inlet ports to said outlet ports such as to permit passage of a fiberoptic bronchoscope therethrough and stop means for limiting the rotation of said valve members to 90°.

10. The adaptor assembly of claim 9 wherein each of said valve members is selectively positionable to a first position for communicating said common central inlet port with one of said outlet ports and to a second position for communicating a lateral inlet port with the respective aligned outlet port.

* * * * *

UNITED STATES PATENT AND TRADEMARK OFFICE
CERTIFICATE OF CORRECTION

PATENT NO. : 4,489,721

DATED : December 25, 1984

INVENTOR(S) : George T. Ozaki, Jonathan L. Benumof and Henrik W. Andersen

It is certified that error appears in the above-identified patent and that said Letters Patent are hereby corrected as shown below:

Column 4, Claim 1, line 52, delete the second occurrence of the word "patient".

Signed and Sealed this

Sixth Day of August 1985

[SEAL]

Attest:

DONALD J. QUIGG

Attesting Officer     Acting Commissioner of Patents and Trademarks

UNITED STATES PATENT AND TRADEMARK OFFICE
CERTIFICATE OF CORRECTION

PATENT NO. : 4,489,721

DATED : December 25, 1984

INVENTOR(S) : George T. Ozaki, et al

It is certified that error appears in the above-identified patent and that said Letters Patent is hereby corrected as shown below:

Column 6, Claim 9, line 1, delete the word "central" and insert therefor -- lateral --.

Signed and Sealed this

Twenty-fourth Day of December 1985

[SEAL]

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,489,721
DATED : December 24, 1984
INVENTOR(S) : GEORGE J. OZAKI, JONATHAN L. BENUMOF
HENRIK W. ANDERSEN It is certified that error appears in the above-identified patent and that said Letters Patent are hereby corrected as shown below:

Claim 9, column 6, line 1, the word "central" is to be replaced with the word --lateral--; and at column 6, line 2, the word "lateral" is to be returned to the original word --central--

This certificate supersedes Certificate of Correction issued December 24, 1985 --.

Signed and Sealed this

Fourth Day of February 1986

[SEAL]

Attest:

DONALD J. QUIGG

Attesting Officer

Commissioner of Patents and Trademarks